US007202050B2

(12) United States Patent
Auld

(10) Patent No.: US 7,202,050 B2
(45) Date of Patent: Apr. 10, 2007

(54) METHODS FOR MEASURING PHOSPHATASE ACTIVITY

(75) Inventor: Douglas Auld, Cranbury, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 0 days.

(21) Appl. No.: 11/100,068

(22) Filed: Apr. 6, 2005

(65) Prior Publication Data

US 2005/0191718 A1    Sep. 1, 2005

Related U.S. Application Data

(62) Division of application No. 10/146,165, filed on May 15, 2002, now Pat. No. 6,942,987.

(51) Int. Cl.
*C12Q 1/42*    (2006.01)
(52) U.S. Cl. .......................... 435/21; 530/323
(58) Field of Classification Search ................ 435/21; 530/323
See application file for complete search history.

(56) References Cited

U.S. PATENT DOCUMENTS

| 5,580,747 | A | * | 12/1996 | Shultz et al. ................ 435/24 |
| 5,981,200 | A | * | 11/1999 | Tsien et al. ................. 435/7.4 |
| 6,037,137 | A |   | 3/2000  | Komoriya et al. ............ 435/23 |
| 6,335,201 | B1 |  | 1/2002  | Allbritton et al. ............ 436/63 |
| 6,942,987 | B2 | * | 9/2005 | Auld ............................ 435/15 |

| 2001/0044117 | A1 |   | 11/2001 | Epps et al. ................. 435/7.1 |
| 2002/0037542 | A1 |   | 3/2002  | Allbritton et al. ......... 435/7.23 |
| 2003/0027236 | A1 | * | 2/2003 | Burke et al. ................. 435/15 |
| 2003/0113768 | A1 | * | 6/2003 | Zweig ........................... 435/6 |
| 2005/0026234 | A1 | * | 2/2005 | Violin et al. ................. 435/21 |

OTHER PUBLICATIONS

Zambrano et al., "Phosphorylation of P1 Serine Inhibits Peptide Bond Sensitivity to Staphylococcus aureus V8 Protease," Archives of Biochemistry and Biophysics, vol. 368, No. 1, Aug. 1, 1999 pp. 207-209.
Matayoshi et al., "Novel fluorogenic substrates for assaying retroviral proteases by resonance energy transfer," Science Feb. 23, 1990; 247(4945):954-8 (Abstract only).

* cited by examiner

*Primary Examiner*—Ralph Gitomer
(74) *Attorney, Agent, or Firm*—Heslin Rothenberg Farley & Mesiti P.C.; Kathy Smith Dias

(57) ABSTRACT

A method for determining the level of kinase activity or phosphatase activity in a sample without the use of antibodies or radioactive labels is disclosed. The method employs a fluorescently-labeled phosphorylatable reporter peptide that is capable of being cleaved by a protease only when the peptide is in an unphosphorylated state. A change in fluorescence characteristics is an indication that the peptide is cleaved and, therefore, in an unphosphorylated state. Thus, the level of protease cleavage, as measured by the fluorescence change, provides a direct measure of phosphatase activity whereas the level of kinase activity is inversely proportion to the level of protease cleavage. The method is particularly well suited to high throughput screening, for example, for screening compounds which modulate kinase or phosphatase activity.

8 Claims, 5 Drawing Sheets

METHODS FOR MEASURING PHOSPHATASE ACTIVITY

CROSS-REFERENCE TO RELATED APPLICATIONS

This application is a divisional of U.S. Ser. No. 10/146,165 filed May 15, 2002, now issued as U.S. Pat. No. 6,942,987, the disclosure of which is incorporated herein by reference.

FIELD OF THE INVENTION

The present invention relates to methods for determining the level of kinase activity or the level of phosphatase activity in a biological sample without the need for antibodies or radioactive labels, and, in addition, to a method of identifying drugs that modulate kinase or phosphatase activity.

BACKGROUND OF THE INVENTION

Protein phosphorylation is a common regulatory mechanism used by cells to selectively modify proteins carrying regulatory signals from outside the cell to the nucleus. The proteins that execute these biochemical modifications are a group of enzymes known as protein kinases. Kinases represent a large family of enzymes with an estimated 1000 different forms present in the human genome. They play an important role in regulation of signal transduction by adding phosphate groups to various proteins in cellular signaling pathways. Depending on the phosphate accepting protein, the addition of a phosphate group may up-regulate or down regulate the signal. The protein kinases come in two general classes that are defined by the particular amino acid that is phosphorylated. These are tyrosine kinases and serine/threonine kinases.

The complementary activity of dephosphorylation is a function of another group of enzymes known as protein phosphatases. Protein phosphatases can be broadly classified into two families, protein serine/threonine (ser/thr) phosphatases (PP) and protein tyrosine (tyr) phosphatases (PTPase). Tyrosine phosphatases generally catalyze the dephosphorylation of tyrosine residues, though some have dual specificity for both phosphoser/thr and phosphotyrosine. Ser/thr phosphatases catalyze the dephosphorylation of phosphoserine and phosphothreonine residues in proteins and peptides and have been further divided into three types, PP1, PP2A and PP2B. PTP/PPases provide reversible protein phosphorylation through the dephosphorylation of phosphoamino acids and function in the control of cellular proliferation, differentiation and other cellular processes. These phosphatases can be classified into soluble or transmembrane proteins.

Kinases and phosphatases are often validated drug targets since human diseases are frequently linked to dysregulation of cellular signaling pathways. The profound cellular effects mediated by tyrosine kinases and serine kinases, for example, their putative role in angiogenesis [Giroux, S. et al. Curr. Biol. 9: 369 (1999)], lymphoid development [Nosaka, T., et al. Science 270: 800, (1995)] and insulin resistance [Yuan, M. et al., Science 293: 1673, (2001)] coupled with the implication that mutant or defective tyrosine kinase variants may be involved in tumorigenesis [Jeffers, M., et al. PNAS 94: 11445, (1997)], have made them attractive targets for the development of new therapeutic molecules.

Methods for measuring the phosphorylation state of cellular proteins have traditionally relied on radioactive means, for example, $^{32}P$ or $^{33}P$-gammaphosphate incorporation or assays employing labeled antibodies. Phosphorylated tyrosine residues, for example, can be detected either by immunoprecipitation or blotting using a radiolabeled antiphosphotyrosine antibody or using filter binding to trap radiolabeled products. The fact that the techniques for detecting radioactive isotope (i.e. blotting, immunoprecipitation, gel electrophoresis) are very time consuming, however, minimizes the appeal of these methodologies for high throughput screening.

More recent methods utilize a standard enzyme-linked immunosorbent assay (ELISA) format for measuring kinase or phosphatase activity. These methods utilize purified heterologous substrate protein or synthetic substrate peptides anchored to a microtiter plate. After exposure of the substrate molecule to a sample containing the appropriate kinase or phosphatase, the level of phosphorylation is evaluated with antiphosphotyrosine antibodies to quantitate the amount of phosphorylated protein bound to the plate. In this method, kinase or phosphatase activity is determined after any unbound antibody is removed from the plate.

Hirth et al., U.S. Pat. No. 5,763,198, for example, describes an ELISA-type assay in which a substrate-specific antibody is used as an anchoring molecule to isolate a protein substrate from a cell lysate preparation and immobilize it on a solid phase support. Hirth's method then determines the level of kinase activity or phosphatase activity by evaluating the tyrosine phosphorylation state of the protein substrate bound to the solid phase. Hirth's method uses an anti-phosphotyrosine antibody as the detecting molecule and the unbound portion of the anti-phosphotyrosine is removed by a plate washing procedure.

A homogenous assay has been described for tyrosine kinases involving the use of a fluorescently labeled peptide and an antibody that is specific for the phosphorylated product. This method employs fluorescence polarization for detection where the antibody/labeled peptide complex possesses a greater polarization signal than the free labeled peptide. Other methods for measuring tyrosine kinase activity, particularly tyrosine kinase receptor activity, are described in WO95/04136, EP 0 730 740 B1, and U.S. Pat. No. 5,599,681.

The availability of an efficient, high throughput assay of kinase activity or phosphatase activity, particularly, one that does not rely on either radioactive labels or antibodies and does not require any separation steps, is highly desirable because it provides the means, not only to determine the level of kinase or phosphatase activity in a sample, but to do so without the limitations associated with the use of radioisotopes and antibodies.

SUMMARY OF THE INVENTION

In one aspect, the invention relates to a method for measuring protein kinase activity in a sample. The method uses a fluorescently-labeled reporter peptide that comprises a protease cleavage site that is phosphorylatable. The method comprises the steps of contacting a sample with the reporter peptide for an amount of time sufficient for phosphorylation of the reporter peptide to occur wherein the reporter peptide is a fluorescently labeled phosphorylatable peptide that is protease-cleavable when unphosphorylated; contacting the reporter peptide, a portion of which is now phosphorylated, with a protease capable of cleaving unphosphorylated peptide, for a time sufficient for proteolysis to occur; and detecting a change in a fluorescence characteristic of the reporter peptide whereby the change indicates kinase activity. Fluorescence quenching (FQ), fluorescence polarization (FP), fluorescence resonance energy transfer (FRET), chemiluminescence-resonance energy transfer (CRET), bioluminescence resonance energy transfer (BRET) and time resolved fluorescence resonance energy transfer (TR-FRET) are examples of fluorescence characteristics to be monitored for changes.

In a related aspect, the invention relates to a method of measuring kinase activity wherein a change in a fluorescence characteristic is detected by a method selected from the group consisting of fluorescence microscopy, flow cytometry, fluorometry and absorption spectroscopy. A fluorescence microplate reader is also suitable for measuring a change in a fluorescence characteristic of the reporter peptide.

In yet another related aspect, the invention relates to a method for screening a substance for the ability to modulate kinase activity comprising the steps: exposing a first portion of a kinase preparation to the substance; determining the level of kinase activity in the first portion by (1) contacting the first portion with a peptide for an amount of time sufficient for phosphorylation of the peptide to occur, wherein the peptide is a fluorescently labeled phosphorylatable peptide that is protease-cleavable when unphosphorylated; (2) contacting this first portion with a protease capable of cleaving unphosphorylated peptide for a time sufficient for maximum proteolysis to occur; and (3) detecting a change in a fluorescence characteristic of the labeled peptide whereby the change in the fluorescence characteristic indicates kinase activity in the first portion; then, repeating steps (1) through (3) for a second portion of the kinase preparation that has not been exposed to the substance and comparing the change in the fluorescence characteristic for the first and second portions.

In a related aspect, the invention relates to a method for screening a substance for the ability to modulate kinase activity, comprising the step of determining the level of kinase activity in the sample and comparing the level with a standard having a known level of kinase activity.

In yet another aspect, the invention relates to a method for determining the level of kinase activity in a sample employing a reporter peptide, wherein the reporter peptide comprises an amino acid sequence selected from the group consisting of DESEEEDK (SEQ ID NO. 1) QKRPSQR (SEQ ID NO.:2), RRRRSIIFI (SEQ ID NO.: 3), $X_n$-SP-$X_n$ (SEQ ID NO.: 4), EEEYEE (SEQ ID NO.: 5), KSPXXXK (SEQ ID NO.: 6), EAVTSPRFI (SEQ ID NO.: 7), HHHRSPRKR (SEQ ID NO.: 8), HHHKSPRRR (SEQ ID NO.: 9), KKRQQSFDMK (SEQ ID NO.: 10), $X_n$-HSR-$X_n$(SEQ ID NO.: 11), RFRRSRRMI (SEQ ID NO.: 12) where X is an amino acid, n is any number 0 or greater.

In a related aspect, the invention relates to a method for determining the level of kinase activity in a sample employing a reporter peptide, wherein the reporter peptide is selected from the group consisting of $(F_1)X_n$- DESEEEDK-$X_n(F_2)$(SEQ ID NO. 1), $(F_1)$-$X_n$-QKRPSQR-$X_n$-$(F_2)$ (SEQ ID NO.:2), $(F_1)$-$X_n$-RRRRSIIFI-$X_n$-$(F_2)$ (SEQ ID NO.: 3), $(F_1)$-$X_n$-EEEYEE-$X_n$-$(F_2)$(SEQ ID NO.:) $X_n$-SP-$X_n$ (SEQ ID NO.: 4), $(F_1)$-$X_n$-KSPXXXK-$X_n$-$(F_2)$ (SEQ ID NO.: 6), $(F_1)$-$X_n$-EAVTSPRFI-$X_n$-$(F_2)$ (SEQ ID NO.: 7), $(F_1)$-$X_n$-HHHRSPRKR -$X_n$-$(F_2)$ (SEQ ID NO.: 8), $(F_1)$-$X_n$-HHHK-SPRRR-$X_n$-$(F_2)$ (SEQ ID NO.: 9), $(F_1)$-$X_n$-KKRQQS-FDMK-$X_n$-$(F_2)$ (SEQ ID NO.: 10), $(F_1)$-$X_n$-HSR-$X_n$-$(F_2)$ (SEQ ID NO.: 11), $(F_1)$-$X_n$-RFRRSRRMI-$X_n$-$(F_2)$ (SEQ ID NO.: 12) where $F_1$ is a first fluorescent label, $F_2$ is a second fluorescent label either the same or different from $F_1$, X is an amino acid, n is any number 0 or greater.

In yet another aspect, the invention relates to a method for measuring protein phosphatase activity in a sample. The method uses a fluorescently-labeled reporter peptide that comprises a protease cleavage site that contains a phospho-amino acid. The method comprises the steps of contacting a sample with the reporter peptide for an amount of time sufficient for dephosphorylation of the reporter peptide to occur wherein the reporter peptide is a fluorescently labeled phospho-peptide that is protease-cleavable when unphosphorylated; contacting the reporter peptide, a portion of which is now dephosphorylated, with a protease capable of cleaving unphosphorylated peptide, for a time sufficient for proteolysis to occur; and detecting a change in a fluorescence characteristic of the reporter peptide whereby the change indicates phosphatase activity. Fluorescence quenching (FQ), fluorescence polarization (FP), fluorescence resonance energy transfer (FRET), chemiluminescence-resonance energy transfer (CRET), bioluminescence resonance energy transfer (BRET) and time resolved fluorescence resonance energy transfer (TR-FRET) are examples of fluorescence characteristics to be monitored for changes.

In a related aspect, the invention relates to a method of measuring phosphatase activity wherein a change in a fluorescence characteristic is detected by a method selected from the group consisting of fluorescence microscopy, flow cytometry, fluorometry and absorption spectroscopy. A fluorescence microplate reader is also suitable for measuring a change in a fluorescence characteristic of the reporter peptide.

In yet another related aspect, the invention relates to a method for screening a substance for the ability to modulate phosphatase activity comprising the steps: exposing a first portion of a phosphatase preparation to the substance; determining the level of phosphatase activity in the first portion by (1) contacting the first portion with a peptide for an amount of time sufficient for dephosphorylation of the peptide to occur, wherein the peptide is a fluorescently labeled phosphorylated peptide that is protease-cleavable when unphosphorylated; (2) contacting this first portion with a protease capable of cleaving unphosphorylated peptide for a time sufficient for maximum proteolysis to occur; and (3) detecting a change in a fluorescence characteristic of the labeled peptide whereby the change in the fluorescence characteristic indicates phosphatase activity in the first portion; then, repeating steps (1) through (3) for a second portion of the phosphatase preparation that has not been exposed to the substance and comparing the change in the fluorescence characteristic for the first and second portions.

In a related aspect, the invention relates to a method for screening a substance for the ability to modulate phosphatase activity, comprising the step of determining the level of phosphatase activity in the sample and comparing the level with a standard having a known level of phosphatase activity.

In yet another aspect, the invention relates to a method for determining the level of phosphatase activity in a sample employing a reporter peptide, wherein the peptide comprises an amino acid sequence selected from the group consisting of DE*SEEEDK (SEQ ID NO. 1) QKRP*SQR (SEQ ID NO.:2), RRRR*SIIFI (SEQ ID NO.: 3), $X_n$-*SP-$X_n$ (SEQ ID NO.: 4), EEE*YEE (SEQ ID NO.: 5), K*SPXXXK (SEQ ID NO.: 6), EAVT*SPRFI (SEQ ID NO.: 7), HHHR*SPRKR (SEQ ID NO.: 8), HHHK*SPRRR (SEQ ID NO.: 9), KKRQQ*SFDMK (SEQ ID NO.: 10), $X_n$-H*SR-$X_n$-(SEQ ID NO.: 11), RFRR*SRRMI (SEQ ID NO.: 12), $X_n$-*Y-$X_n$ (SEQ ID NO. 13), $X_n$-KDDE*YNPA-$X_n$ (SEQ ID NO. 14), $X_n$-RFDRRZ*SV-$X_n$-(SEQ ID NO. 15), X-RRREEEE*TEEE-$X_n$ (SEQ ID NO. 16), $X_n$-MHRQE*TVD$X_n$ (SEQ ID NO. 17), where Z=V, I, L or F, where *S is phosphoserine, *Y is phosphotyrosine, X is an amino acid, n is any number 0 or greater.

In a related aspect, the invention relates to a method for determining the level of phosphatase activity in a sample employing a reporter peptide, wherein said reporter peptide is selected from the group consisting of $(F_1)X_n$-DE*SEEEDK-$X_n(F_2)$(SEQ ID NO. 1), $(F_1)$-$X_n$-QKRP*SQR-$X_n$-$(F_2)$ (SEQ ID NO.:2), $(F_1)$-$X_n$-RRRR*SIIFI-$X_n$-$(F_2)$ (SEQ ID NO.: 3), $(F_1)$-$X_n$-EEE*YEE-$X_n$-$(F_2)$(SEQ ID NO.:) $X_n$-*SP-$X_n$ (SEQ ID NO.: 4), $(F_1)$-$X_n$-K*SPXXXK-$X_n$-$(F_2)$ (SEQ ID NO.: 6), $(F_1)$-$X_n$-EAVT*SPRFI-$X_n$-$(F_2)$ (SEQ ID NO.: 7), $(F_1)$-$X_n$-HHHR*SPRKR -$X_n$-$(F_2)$ (SEQ ID NO.: 8), $(F_1)$-$X_n$-HHHK*SPRRR-$X_n$-$(F_2)$ (SEQ ID NO.: 9), $(F_1)$-$X_n$-KKRQQ*SFDMK-$X_n$-$(F_2)$ (SEQ ID NO.: 10), $(F_1)$-$X_n$-H*SR-$X_n$-$(F_2)$ (SEQ ID NO.: 11), $(F_1)$-$X_n$-RFRR*SRRMI-$X_n$-$(F_2)$ (SEQ ID NO.: 12), $(F_1)$-$X_n$-*Y-$X_n$-$(F_2)$ (SEQ ID NO. 13), $(F_1)$-$X_n$-KDDE*YNPA-$X_n$-$(F_2)$ (SEQ ID NO. 14), $(F_1)$-$X_n$-RFDRRZ*SV-$X_n$-$(F_2)$ (SEQ ID NO. 15), $(F_1)$-$X_n$-RRREEEE*TEEE-$X_n$-$(F_2)$ (SEQ ID NO. 16), $(F_1)$-X-MHRQE*TVD$X_n$-$(F_2)$ (SEQ ID NO. 17), where Z=V, I, L or F where *S is phosphoserine, *Y is phosphotyrosine, $F_1$ is a first fluorescent label, $F_2$ is a second fluorescent label, X is an amino acid, n is any number 0 or greater.

In a yet another related aspect, the invention relates to a composition of the formula:

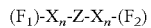

where $F_1$ is a first fluorescent label, $F_2$ is a second fluorescent label, X is an amino acid, Z is a peptide, and n is any number 0 or greater. The peptide comprises an amino acid sequence selected from the group consisting of DE*SEEEDK (SEQ ID NO. 1) QKRP*SQR (SEQ ID NO.:2), RRRR*SIIFI (SEQ ID NO.: 3), $X_n$-*SP-$X_n$(SEQ ID NO.: 4), EEE*YEE (SEQ ID NO.: 5), K*SPXXXK (SEQ ID NO.: 6), EAVT*SPRFI (SEQ ID NO.: 7), HHHR*SPRKR (SEQ ID NO.: 8), HHHK*SPRRR (SEQ ID NO.: 9), KKRQQ*SFDMK (SEQ ID NO.: 10), $X_n$-H*SR-$X_n$-(SEQ ID NO.: 11), RFRR*SRRMI (SEQ ID NO.: 12), $X_n$-*Y-$X_n$ (SEQ ID NO. 13), $X_n$-KDDE*YNPA-$X_n$(SEQ ID NO. 14), $X_n$-RFDRRB*SV-$X_n$-(SEQ ID NO. 15), X-RRREEEE*TEEE-$X_n$ (SEQ ID NO. 16), $X_n$-MHRQE*TVD$X_n$(SEQ ID NO. 17), where B=V, I, L or F, *S is phosphoserine, *Y is phosphotyrosine, X is an amino acid, n is any number 0 or greater.

The may be selected from $(F_1)X_n$-DE*SEEEDK-$X_n(F_2)$ (SEQ ID NO. 1), $(F_1)$-$X_n$-QKRP*SQR-$X_n$-$(F_2)$ (SEQ ID NO.:2), $(F_1)$-$X_n$-RRRR*SIIFI-$X_n$-$(F_2)$ (SEQ ID NO.: 3), $(F_1)$-$X_n$-EEE*YEE-$X_n$-$(F_2)$(SEQ ID NO.:) $X_n$-*SP-$X_n$(SEQ ID NO.: 4), $(F_1)$-$X_n$-K*SPXXXK-$X_n$-$(F_2)$ (SEQ ID NO.: 6), $(F_1)$-$X_n$-EAVT*SPRFI-$X_n$-$(F_2)$ (SEQ ID NO.: 7), $(F_1)$-$X_n$-HHHR*SPRKR-$X_n$-$(F_2)$ (SEQ ID NO.: 8), $(F_1)$-$X_n$-HHHK*SPRRR-$X_n$-$(F_2)$(SEQ ID NO.: 9), $(F_1)$-$X_n$-KKRQQ*SFDMK-$X_n$-$(F_2)$ (SEQ ID NO.: 10), $(F_1)$-$X_n$-H*SR-$X_n$-$(F_2)$ (SEQ ID NO.: 11), $(F_1)$-$X_n$-RFRR*SRRMI-$X_n$-$(F_2)$ (SEQ ID NO.: 12), $(F_1)$-$X_n$-*Y-$X_n$-$(F_2)$ (SEQ ID NO. 13), $(F_1)$-$X_n$-KDDE*YNPA-$X_n$-$(F_2)$ (SEQ ID NO. 14), $(F_1)$-$X_n$-RFDRRB*SV-$X_n$-$(F_2)$ (SEQ ID NO. 15), $(F_1)$-$X_n$-RRREEEE*TEEE-$X_n$-$(F_2)$ (SEQ ID NO. 16), $(F_1)$-$X_n$-MHRQE*TVD$X_n$-$(F_2)$ (SEQ ID NO. 17), where B=V, I, L or F where *S is phosphoserine, *Y is phosphotyrosine, $F_1$ is a first fluorescent label, $F_2$ is a second fluorescent label, X is an amino acid, n is any number 0 or greater.

DETAILED DESCRIPTION OF THE INVENTION

Figure 1:
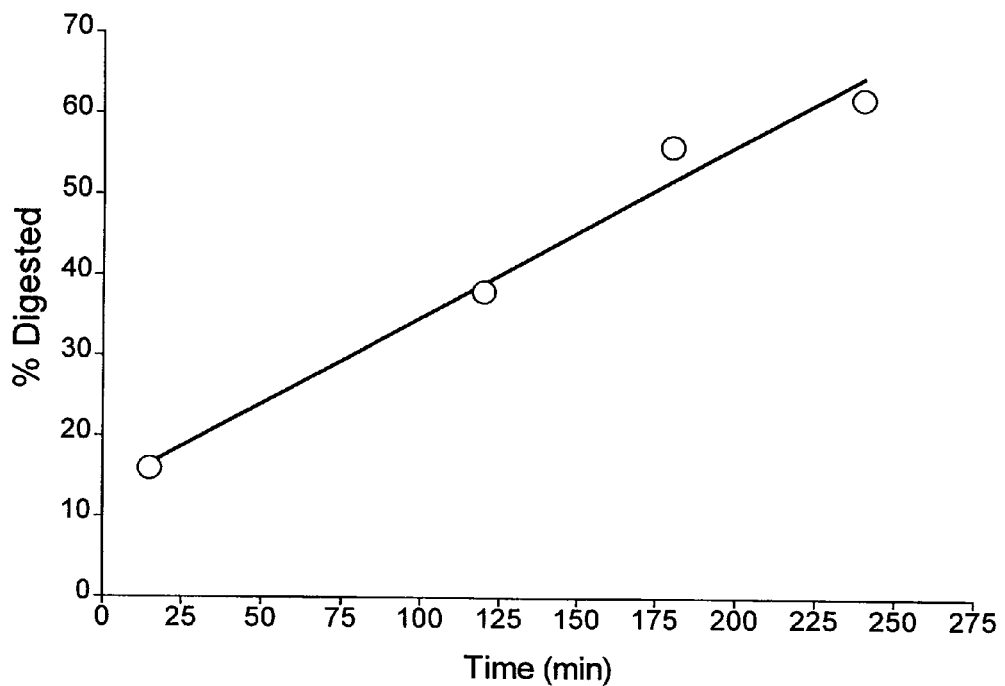
FIG. 1 is a graph depicting the cleavage of casein kinase II (CKII) substrate peptide by V8 protease over time.

All patents, applications, publications, or other references that are listed herein are hereby incorporated by reference. In the description that follows, certain conventions will be followed as regards the usage of terminology:

The term "peptide", as it is commonly understood in the art, refers to a molecule of about 10 kilodaltons (kDa) or less which is a polyamide of α-amino acids. For purposes of practicing the present invention, peptides may be obtained by proteolytic digestion of the protein of interest, chemically synthesized or produced by recombinant technology.

The term "phosphorylatable" in reference to a peptide, indicates that the peptide contains at least one tyrosine, serine, threonine or histidine residue capable of being phosphorylated under the appropriate conditions, i.e., in the presence of a kinase and a high energy phosphate source.

The term "sample" or "biological sample" refers to any source of kinase activity and is intended to encompass purified kinase preparations, cells, both whole and fractionated, cell and tissue extracts, and bodily fluids, for example, urine, serum, plasma and the like.

The term "protease binding site" is used herein to refer to an amino acid sequence that is characteristically recognized and cleaved by a protease.

A "fluorophore" is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators within the lanthanide ion series. A fluorophore is distinguished from a chromophore which absorbs, but does not characteristically re-emit light.

The term "residue" or "amino acid residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The terms "protease activity" or "activity of a protease" refer to the cleavage of a peptide by a protease. Protease activity comprises the hydrolysis of one or more peptides into smaller peptide fragments. Protease activity of a particular protease usually results in hydrolysis at particular peptide binding sites characteristically recognized by the particular protease. The particular protease may be characterized by the production of peptide fragments bearing particular terminal amino acid residues.

The term "fluorescence characteristic" refers to one or more parameters by which the fluorescence of a fluorescent molecule is characterized. Most frequently the parameter measured is fluorescence intensity. Measurement of other parameters of fluorescence, however, including but not limited to fluorescence quenching, polarization, absorption and the like, are intended to be encompassed by the method of the invention. See Lakowicz, J. R., *Principles of Fluorescence Spectroscopy*, Plenum Press, New York, 1983 and Slavik, J., *Fluorescent Probes in Cellular and Molecular Biology*, CRC Press, Boca Raton, 1993 which are incorporated herein by reference.

In accordance with the method of the present invention, the level of kinase activity in a sample can be determined by contacting the sample with a phosphorylatable reporter peptide such as the one described herein. Similar reporter peptides have been described for use in measuring the level of protease activity (U.S. Pat. Nos. 5,981,200 and 6,037,137, the contents of which are hereby incorporated by reference.) Some portion of the reporter peptide, which contains a phosphorylatable amino acid residue, becomes phosphorylated as a result of kinase activity present in the sample to which the reporter peptide is exposed. Subsequently, the reporter peptide is contacted with a protease capable of cleaving the peptide when it is in its unphosphorylated state. The extent to which cleavage of the peptide has occurred is indicated by a change in fluorescence properties that results from cleavage of the peptide. The level of kinase activity can then be extrapolated from the degree of proteolysis of the peptide.

Conversely, the level of phosphatase activity in a sample can be determined using a reporter peptide in which the phosphorylatable amino acid residue is in its phosphorylated state, i.e., the reporter peptide contains a phosphoserine, phosphotyrosine etc. In this assay, the removal of the phosphate by the phosphatase enables the reporter to be cleaved by the cognate protease. As a result, a change in a fluorescence characteristic of the reporter peptide, for example, fluorescence intensity, is directly proportional to the level of phosphatase activity in the sample.

This invention provides for the determination of the level of kinase or phosphatase activity in a sample using fluorescently-labeled reporter peptides which are protease cleavable in the unphosphorylated state but are no longer cleavable when phosphorylated. The fluorogenic reporter peptides described herein generally comprise a first fluorescent label, (for example, a donor fluorophore) linked to a second fluorescent label by a peptide comprising an amino acid sequence that is (a) phosphorylatable and (b) recognized and cleaved by a particular protease when the peptide is unphosphorylated.

Reporter molecules useful for practicing the methods of the present invention, therefore, have the general formula:

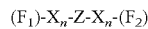

in which Z is a phosphorylatable peptide comprising a protease binding site consisting of 2 to about 12, preferably 2 to about 10, more preferably 2 to about 8, most preferably 2 to about 6, or 2 to about 4 amino acids; $F_1$ and $F_2$ are fluorophores, either the same or different; $X_n$ is a peptide spacer ranging in length from 1 to about 4 amino acids. The design of the reporter molecule involves three components: (1) identification of a minimal sequence required for accepting a phosphate; (2) identifying a protease that is capable of cleaving the peptide; (3) adding appropriate labels to the peptide for detection.

The amino acid sequence of the peptide portion of the reporter molecule in accordance with the present invention comprises a phosphorylatable amino acid residue, that is, one that is capable of accepting a phosphate moiety (e.g., serine, threonine, tyrosine or histidine), appropriate recognition elements for a kinase or phosphatase of interest, appropriate recognition elements for a protease and sites to allow labeling of the peptide with fluorophores.

The peptide may be generated by any standard means known to those of skill in the art including by proteolytic digestion of the protein substrate for the kinase of interest, chemical synthesis or as the product of recombinant technology.

Identification of Kinase Substrate Sequence

Determination of kinase substrate specificity is not particular to the technology described herein, since this is common to all kinase assay formats. For many kinases such minimal sequences have been defined and have been divided into classes that contain basic, acidic or neutral residues (Sonyang, Z. et al. (1996) Molecular and Cellular Biology 16: 6486–6493). Songyang, Z. et al. (1994) Current Biology 4:973–982). One of skill in the art will recognize that other peptide sequences can be designed for any kinase once its recognition sequence is defined. Functionally equivalent peptides include but are not limited to those peptides containing additions, deletions or substitutions of like amino acid residues within the kinase recognition sequence. Amino acid substitutions may be made on the basis of similarity in polarity, charge, solubility, size, hydrophobicity, hydrophilicity, and/or the amphipathic nature of the residues involved. For example, nonpolar (hydrophobic) neutral amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

If no information is available about the cognate substrate for a particular kinase of interest, then the class of the substrate can be determined by homology of the kinase to known kinases. Alternatively, the kinase can be tested against a panel of known substrates to determine its class specificity. Knowing the class specificity of the kinase then permits the identification of a suitable substrate peptide.

In some instances, a generic sequence can be used that provides activity across a particular class of kinases, for example, the employment of polyglutamate/tyrosine as substrate for tyrosine kinases.

Identification of Protease

A protease binding site, generally, is an amino acid sequence that is recognized and cleaved by a particular protease. It is well known that various proteases cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The prolyl endoprotease (PEP) cleaves peptide bonds next to proline.

Conveniently, since protease recognition sequences are also divided into acidic, basic and neutral containing residues, certain residues will be common to both the recognition sequence of the kinase of interest and a protease recognition sequence. For example, there is a class of kinases that phosphorylate Ser/Thr N-terminal to proline residues (e.g., p42$^{MAPK}$ and p44$^{MAPK}$) and the PEP class of proteases recognize sequences such as Ser/Thr-Pro and Pro-Ser/Thr. Additionally, certain cellular systems are known which use a kinase/protease pair to regulate the system and this information can also be used in designing appropriate peptides. For example, the cellular substrate vimentin contains a recognition site for the ser kinase PKC. This site is also a cleavage site for HIV type 1 proteinase and this cleavage is critical to the life cycle of the virus. Therefore, the retroviral life cycle can be regulated by proteolytic processing that is attenuated by phosphorylation. Examples of a number of kinase/protease detection partners are given below in Table 1.

TABLE 1

KINASE AND PROTEASE DETECTION PAIRS

| KINASE | PROTEASE |
| --- | --- |
| Acidic | Endoprotease Glu-C (V8 protease) |
| Casein kinase I (CKI) | |
| Casein kinase II (CKII) | |
| Basic | |
| PKA | Endoprotease Lys-C or Arg-C |
| NIMA | |
| SLK1 | |
| CGPK | |
| SRPK2 | |
| Neutral (or proline directed) | |
| MAPK family | Elastase or prolyl endoprotease |
| CDK isoforms | |
| PKC isoforms | |
| c-Jun | |
| Akt2 | |
| PKC isoforms | |
| CamKII | |
| Tyrosine kinases | |
| Receptor linked or cytosolic | Chymotrypsin |
| Src | |
| Lyn | |
| Lck | |
| c-Abl | |
| Zap 70 | |
| EGF receptor | |
| PDGF receptor | |
| FGF receptor | |
| Insulin receptor | |

Table 2 provides examples of representative reporter peptides and proteases useful for determining the level of kinase activity in a sample for a particular kinase of interest.

TABLE 2

| Kinase | Reporter Peptide Molecule | Protease |
| --- | --- | --- |
| PKC | (F$_1$)-X$_n$-QKRPSQR-X$_n$-(F$_2$)(SEQ ID NO. 2)[a] | prolyl endoprotease |
| PKA | (F$_1$)-X$_n$-RRRSIIFI-X$_n$-(F$_2$)(SEQ ID NO. 3) | Endoprotease Arg-C |
| MAPK | (F$_1$)-X$_n$-SP-X$_n$-(F$_2$)(SEQ ID NO. 4) | Elastase or prolyl endoprotease |
| CKII | (F$_1$)X$_n$-DESEEEDK-X$_n$(F$_2$) (SEQ ID NO. 1) | V8 protease |
| tyrosine kinase | (F$_1$)-X$_n$-E$_q$YE$_q$-X$_n$-(F$_2$) where q is any number > 0 e.g., (F$_1$)-X$_n$-EEEYEE-X$_n$-(F$_2$)(SEQ ID NO. 5). | Chymotrypsin |

TABLE 2-continued

| Kinase | Reporter Peptide Molecule | Protease |
| --- | --- | --- |
| ERK1/2 | (F$_1$)-X$_n$-KSPXXXK-X$_n$-(F$_2$)(SEQ ID NO. 6)[d] | prolyl endoprotease |
| ERK1 | (F$_1$)-X$_n$-EAVTSPRFI-X$_n$-(F$_2$)(SEQ ID NO. 7)[c] | prolyl endoprotease |
| CyclinA/CDK2 | (F$_1$)-X$_n$-HHHRSPRKR-X$_n$-(F$_2$)(SEQ ID NO. 8)[b] | prolyl endoprotease |
| Cyclin B/CDC2 | (F$_1$)-X$_n$-HHHKSPRRR-X$_n$-(F$_2$)(SEQ ID NO. 9)[b] | prolyl endoprotease |
| CamKII | (F$_1$)-X$_n$-KKRQQSFDMK-X$_n$-(F$_2$)(SEQ ID NO. 10)[c] | Elastase |
| SRPK2 | (F$_1$)-X$_n$-HSR-X$_n$-(F$_2$)(SEQ ID NO. 11)[c] | Arg-C |
| NIMA | (F$_1$)-X$_n$-RFRRSRRMI-X$_n$-(F$_2$)(SEQ ID NO. 12)[c] | Arg-C |

[a]Yasuda et al. (1990) Biochem. Biophys. Res. Commun. 3: 1220–1227;
[b]Songyang, Z. et al. (1994) Current Biology 4: 973–982;
[c]Songyang, Z. et al. (1996) Molecular and Cellular Biology 16: 6486–6493;
[d]Amin, N. D. et al. (1998) J. Neuroscience 18: 4008–4021.

Labels

For preparation of a reporter molecule useful for practicing the method of the invention, suitable fluorescent labels include rhodamine and rhodamine derivatives, for example, rhodamine X acetamide, 5- and/or 6-carboxytetramethylrhodamine; fluorescein and fluorescein derivatives, coumarins, BODIPY, Alexa Fluorophores (Molecular Probes), Texas Red and cyanine dyes, Dabcyl/Edans pairs or QSY7 paired with blue, green or red fluorophores and chelators within the lanthanide ion series. Additionally, bioluminescence or chemiluminescence can be achieved by incorporating green-fluorescent protein/luciferase pairs or green-fluorescent/aequorin in the presence of calcium. These and other fluorophores, whose suitability for particular applications are well known to the skilled artisan, are commercially available from a large number of manufacturers such as Molecular Probes (Eugene, Oreg.) or Perkin Elmer (Wellesley, Mass.).

The fluorogenic reporter peptide of the present invention is preferably prepared by first synthesizing the desired peptide or obtaining it from a commercial source. The fluorophores are then chemically conjugated to the peptide either directly or via a linker.

If the peptide is to be synthesized de novo, solid phase peptide synthesis in which the C-terminal amino acid of the sequence is attached to an insoluble support followed by sequential addition of the remaining amino acids in the sequence is a preferred method for preparing the peptide backbone of the compounds of the present invention. Techniques for solid phase synthesis are well known to those of skill in the art and are described in detail in the following references: Bodanszky and Bodanszky, Reactivity and Structure Concepts in Organic Chemistry; *Principles of Peptide Synthesis*. Vol. 21; Bodanszky and Bodanszky, The Practice of Peptide Synthesis; *Principles of Peptide Synthesis*. Vol. 16, Springer Verlag, N.Y. (1984); Barany and Merrifield, Solid-Phase Peptide Synthesis; pp. 3–284 in *The Peptides: Analysis, Synthesis, Biology*. Vol. 2: Special Methods in Peptide Synthesis, Part A., Merrifield, et al. J. Am. Chem. Soc. 85, 2149–2156 (1963), and Gross and Meienhofer, eds. Academic press, N.Y., 1980 and Stewart et al., *Solid Phase Peptide Synthesis*, 2nd ed. Pierce Chem. Co., Rockford, Ill. (1984) which are incorporated herein by reference. Solid phase synthesis is most easily accomplished with commercially available peptide synthesizers utilizing FMOC or TBOC chemistry. Phosphopeptides may easily be prepared using this method.

Alternatively, the peptide component of the fluorogenic reporter peptide of the present invention may be synthesized utilizing recombinant DNA technology. Where the reporter peptide is to be used for the measurement of phosphatase activity, a peptide prepared by recombinant technology must be phosphorylated by conventional methods either before or subsequent to the addition of fluorescent labels.

Briefly, for preparing a peptide by recombinant technology, a DNA molecule encoding the desired amino acid sequence is synthesized chemically by a variety of methods known to those of skill in the art including the solid phase phosphoramidite method described by Beaucage and Carruthers, Tetra. Letts. 22: 1859–1862 (1981), the triester method according to Matteucci, et al., J. Am. Chem. Soc., 103:3185 (1981), both incorporated herein by reference, or by other methods known to those of skill in the art.

The oligonucleotides may be purified, if necessary, by techniques well known to those of skill in the art. Typical purification methods include, but are not limited to gel electrophoresis, anion exchange chromatography (e.g. Mono-Q column, Pharmacia-LKB, Piscataway, N.J., USA), or reverse phase high performance liquid chromatography (HPLC). Method of protein and peptide purification are well known to those of skill in the art. For a review of standard techniques see, *Methods in Enzymology* Volume 182: Guide to Protein Purification, M. Deutscher, ed. (1990), pages 619–626, which are incorporated herein by reference.

The oligonucleotides may be converted into double stranded DNA either by annealing with a complementary oligonucleotide or by polymerization with a DNA polymerase. The DNA may then be inserted into a vector under the control of a promoter and used to transform a host cell so that the cell expresses the encoded peptide sequence. Methods of cloning and expression of peptides are well known to those of skill in the art. See, for example, Sambrook, et al., *Molecular Cloning: A Laboratory Manual* (2nd Ed., Vols. 1–3, Cold Spring Harbor Laboratory (1989)), *Methods in Enzymology*, Vol. 152: Guide to Molecular Cloning Techniques (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), which are incorporated herein by reference.

Linkage of the Fluorophores to the Peptide Backbone

The fluorophores are linked to the peptide backbone by any of a number of means well known to those of skill in the art. In one embodiment, the fluorophore is linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. For conjugation to thiols, idoacetamide, maleimide or methyl bromide fluorophore derivatives can be used. For conjugation to amines, succinimidyl esters, sulfonyl chlorides or aldhehyde derivatives can be used. For carboxylic acids, hydrazine and carbodiimides derivatives are available. Similarly, a variety of amine and thiol reactive biotinylation reagents are commercially available. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art.

Detection Methods

Fluorescence detection frequently offers the advantage of using homogeneous assay formats. Any fluorophore whose signal changes upon cleavage of the peptide by the protease may be used in practicing the method of the invention. Most frequently, the fluorescence parameter to be measured is fluorescence intensity. However, changes in other fluorescence characteristics, such as, fluorescence quenching (FQ), fluorescence polarization (FP), fluorescence resonance energy transfer (FRET) and variations thereof including, chemiluminescence-resonance energy transfer (CRET), bioluminescence resonance energy transfer (BRET) and time resolved fluorescence resonance energy transfer (TR-FRET), are also encompassed by the method of the invention. These fluorescence phenomena and methods employed to detect them are generally used to obtain structural maps of complex biological structures, for example, proteins, and other macromolecular assemblies including ribosomes and nucleosomes and are well known to those of skill in the art.

Fluorescence detection methods suitable for use in the method of the present invention include conventional fluorometry, fluorescence microscopy, including confocal microscopy, flow cytometry and absorption spectroscopy. For high throughput screening, laser scanning imaging and microplate fluorescence readers are also suitable.

The reporter peptide molecule used to practice the method of the invention comprises one or two fluorophores. The donor fluorophore typically is excited by incident radiation at a particular wavelength which it then re-emits at a different wavelength which can excite the acceptor fluorophore which may in turn re-emit light of yet a different wavelength. The method of the present invention exploits the relationship between the physical proximity of the fluorophores and their fluorescence characteristics. The protease binding site of the reporter molecule described herein is only cleavable when it is in an unphosphorylated state. Therefore, if the sample contains kinase activity, the amount of protease cleavage will be reduced; the amount of protease activity is inversely proportional to the amount of kinase activity in the sample and can be measured by a change in fluorescence.

In one embodiment, when a donor fluorophore is held in close proximity to the acceptor molecule, the acceptor absorbs the light re-emitted by the donor fluorophore thereby quenching the fluorescence signal of the donor molecule while increasing the fluorescence of the acceptor molecule by energy-transfer. Therefore, by monitoring at the wavelength at which the acceptor emits light, a decrease in fluorescence is observed when the peptide linking the two fluorophores is cleaved by the protease. Alternatively, if the donor wavelength is monitored, an increase in fluorescence is observed when the peptide linking the two fluorophores is cleaved by the protease. The level of kinase activity can then be measured using either the donor or the acceptor wavelength.

In another embodiment, the reporter peptide could be made to contain a fluorophore and a quencher molecule in close proximity. In this case, the re-emitted light from the fluorophore is quenched when the peptide is intact. Upon cleavage with the protease, an increase in fluorescence is observed. Hence, cleavage of the peptide and, therefore, increased fluorescence, is optimal in the absence of kinase activity. The level of fluorescence obtained, therefore, provides an inverse indication of the level of kinase activity present in the sample.

In another embodiment, the reporter peptide could be made to contain a fluorophore and biotin. In this case, the fluorescence polarization of the peptide is measured by the addition of streptavidin after the kinase and protease reaction has been completed. The interaction of streptavidin and biotin is one of the strongest interactions known in biological systems. As fluorescence polarization is proportional to the molecular weight one will observe, an increase in polarization signal when the biotinylated peptide containing the fluorophore binds to streptavidin. However, if the fluorophore and biotin are separated by protease cleavage of the peptide, the fluorescence polarization does not increase upon the addition of streptavidin. Hence, the fluorescence polarization signal is directly proportional to the level of kinase activity in the sample.

In another embodiment, the reporter peptide could be made to contain a fluorophore and biotin. In this case the fluorophore is a cyanine dye and laser scanning confocal microscopy is used to image streptavidin micro-beads coated with the cyanine labeled biotinylated peptide. The fluorescent signal of each micro-bead is then quantified. If the cyanine is separated from the micro-bead by protease cleavage of the peptide, the fluorescent signal of each bead is decreased. Hence, the fluorescent signal is directly proportional to the level of kinase activity in the sample.

In another embodiment, the reporter peptide could be made to contain lanthanides. In this case, the reporter peptide is constructed by incorporating a lanthanide at one end of the peptide and biotin on the other. A TR-FRET signal can be obtained by the additional of allophycocyanin-labeled streptavidin provided that the biotionylated peptide contains the lanthanide. If the lanthanide and the biotin are separated by protease cleavage, then the TR-FRET signal is decreased. Hence, the TR-FRET signal is directly proportional to the level of kinase activity in the sample.

In another embodiment, the reporter peptide can be made with recombinantly expressed proteins that are able to emit bioluminescence. In this example, a peptide containing an appropriate kinase site and a specific protease site is used to link green fluorescence protein and luciferase protein in close proximity. Alternatively, green fluorescent protein and aequorin can be used. When the two proteins are separated by protease cleavage, the bioluminescence decreases. Hence, the bioluminescence signal is directly proportional to the level of kinase activity in the sample.

Kinase Assay

Human casein kinase II (CKII) is a serine/threonine kinase for which only a radioactive SPA assay has been previously described. In one embodiment, the method of the present invention uses a fluorescently labeled peptide that is recognized by CKII and V8 protease (endo-protease Glu-C) which makes it possible to measure CKII in a non-radioactive low-volume assay format (e.g.<5 μl) that is antibody independent.

For practicing the method of the present invention, the following substrate peptide for casein kinase II:

Asp-Glu-Ser-Glu-Glu-Glu-Asp-Lys   (SEQ ID NO.: 1)

was conjugated to tetramethylrhodamine (TMR) and fluoroscein (Flsn) by methods known to those of skill in the art. The resulting reporter peptide was designed:

(SEQ. ID. NO. 1)
TMR-Asp-Glu-Ser-Glu-Glu-Glu-Asp-Lys(Nε-Flsn)-COOH

All peptides showed greater than 90% purity by HPLC and showed the expected molecular weight as determined by mass spectrometry. Endoprotease Glu-C (V8 protease) was purchased from CalBiochem. (San Diego, Calif.). Casein kinase II was purchased from New England BioLabs (Beverly, Mass.). Porcine heparin (approximate MW 6000) was obtained from Sigma (St. Louis, Mo.). ATP was obtained from GibcoBRL (Rockville, Md.). All other reagents were analytical grade.

The ability of V8 protease to cleave the CKII substrate peptide was initially confirmed using HPLC analysis on a reverse phase column (VyDac cat# 218TP54; stationary phase C-18). The peptide (30 μM) was incubated at room temperature with V8 protease (0.1 units) in a buffer containing 20 mM Tris-HCl, 50 mM KCl, 10 mM $MgCl_2$, pH 7.5 (CKII buffer) and aliquots were removed at various time points and flash-frozen in a dry-ice/methanol bath. Products of the protease digestion were then separated on the HPLC column using a 0% to 50% acetonitrile/water gradient in the presence of 0.1% TFA. Peptide was detected using both absorbance at 250 nm and by fluorescence of the rhodamine label using 530 nm excitation and 590 nm emission filters. The results are shown in FIG. 1.

Figure 2:
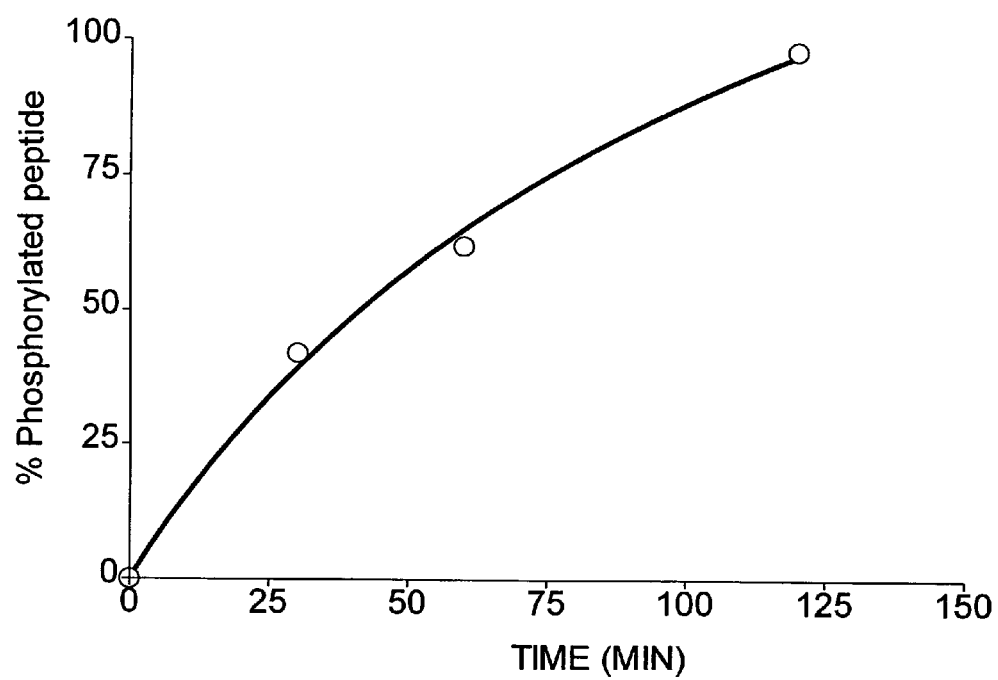
FIG. 2 is a graph depicting the percent of peptide phosphorylated over time by casein kinase II.

Phosphorylation of the peptide by CKII was confirmed by incubation of the peptide with kinase using the above buffer. In general, 30 μM peptide and 40 units of CKII were incubated at 30° C. Aliquots were taken at various time points and flash-frozen in a dry ice/methanol bath; the samples were subsequently analyzed by HPLC under conditions as described above. The results are shown in FIG. 2.

Figure 3:
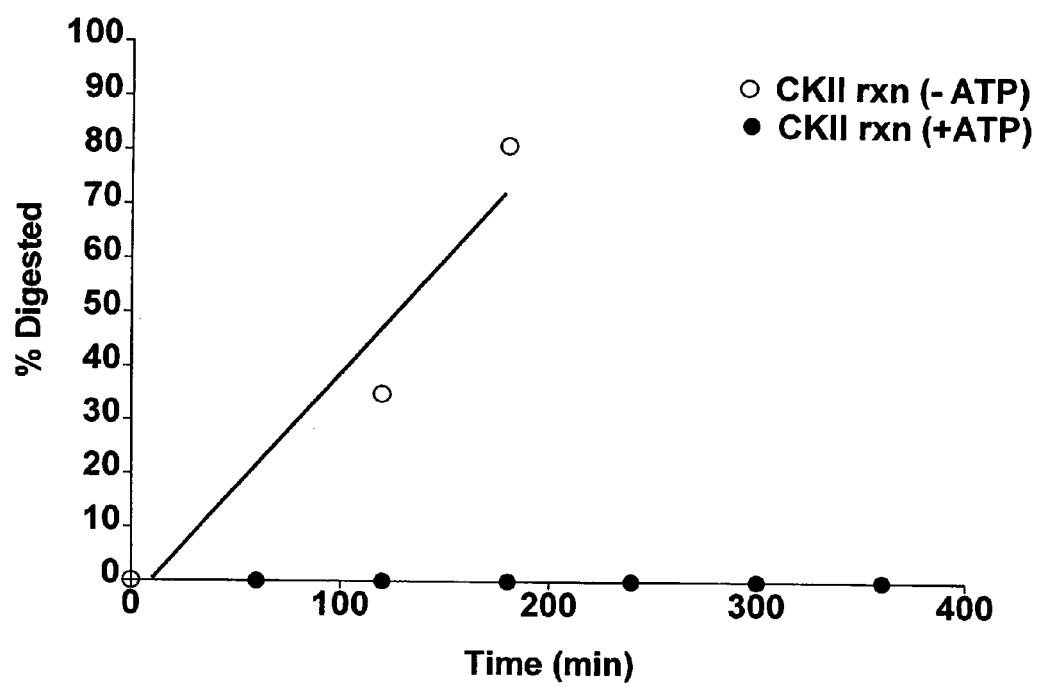
FIG. 3 is a graph depicting protection against V8 digestion by casein kinase II mediated phosphorylation of the peptide. CKII was incubated with peptide in the presence (●) and absence (○) of ATP.

Confirmation that phosphorylation of the peptide prevents V8 protease digestion was shown by first incubating 30 μM peptide with 40 units of CKII for 18 hrs at 30° C. in the presence and absence of ATP (200 μM). Subsequently, 1 unit of V8 protease was added to each sample and the samples were incubated at room temperature. Aliquots were removed at various time points and flash-frozen in a dry-ice/methanol bath for HPLC analysis as described above. HPLC analysis revealed that the phosphorylated peptide is not cleaved by V8 protease after prolonged exposure to the protease while the unphosphorylated peptide is 80% digested in less than three hours (FIG. 3).

Figure 4:
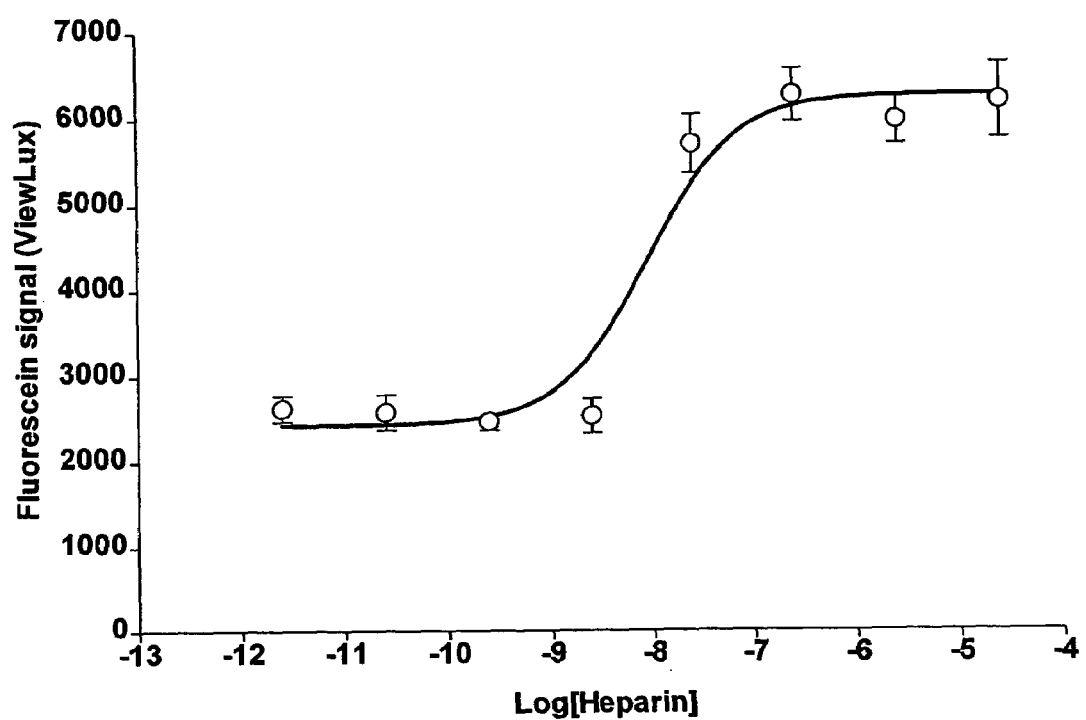
FIG. 4 is a graph depicting resonance energy transfer values for the fluorescein and rhodamine labels vs. heparin concentration.
Figure 5:
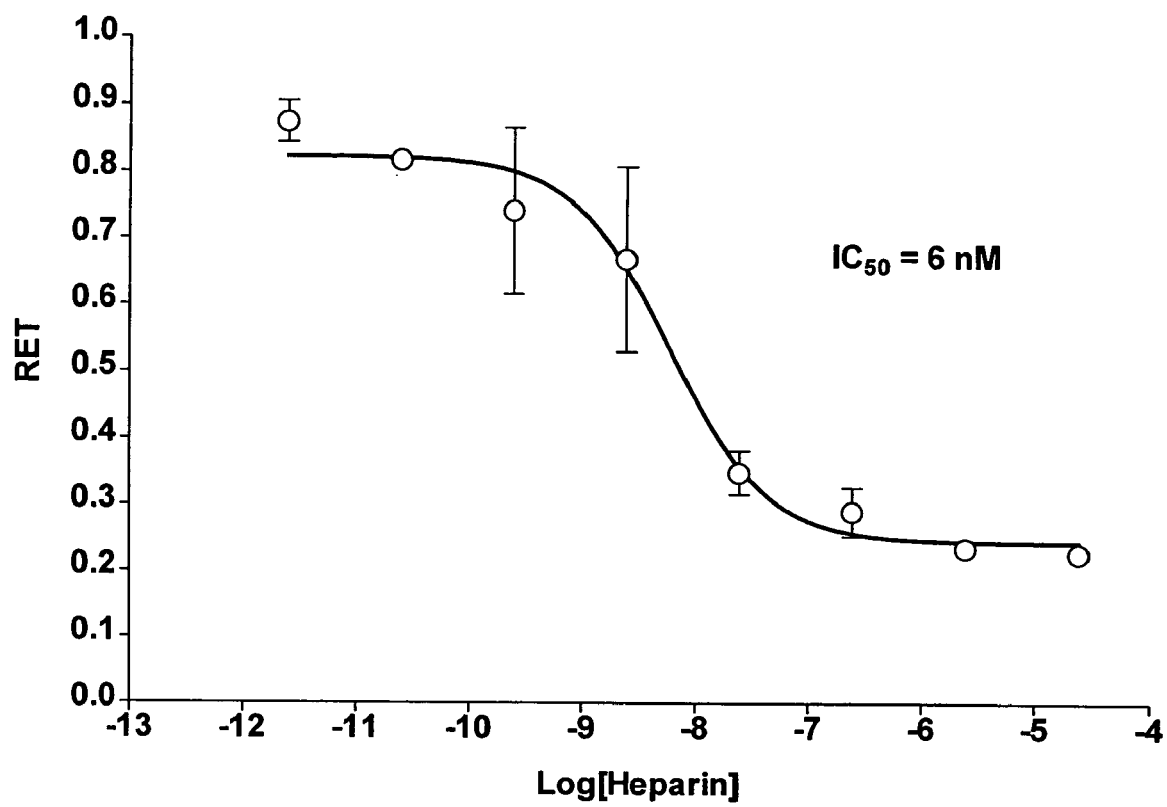
FIG. 5 is a graph depicting fluorescein signal vs. heparin concentration.

A low-volume microtiter plate assay was performed as follows. 1 μL of a peptide in accordance with the present invention, at a concentration of 15 μM in CKII buffer was pipetted into a Greiner white walled 1536 well plate. 1 μL of 600 μM ATP containing various concentrations of heparin was added to the plate. The reaction was started by adding 1 μL of CKII buffer containing 6.5 units of CKII to each well. The final conditions, therefore, were 5 μM peptide, 6.5 units of CKII and 200 μM ATP contained in 3 μL. After incubation for 30 to 45 minutes at 30° C., the kinase reaction was stopped by adding 1 μL of 250 mM EDTA followed by addition of 1 μL of V8 protease (from 0.1 to 0.01 units/well). The digestion was allowed to proceed at room temperature for 5 to 18 hrs. Kinase activity was then detected by reading the plate on a fluorescent plate reader such as the Wallac Victor V or the Wallac ViewLux (E.G.& G. Wallac, Inc., Turku, FI). The change in fluorescence signal relative to heparin concentration is shown in FIG. 4. Resonance energy transfer values (RET) were calculated as described in Litwin et al. (1996) J. Virology 70: 6437–6441 and also correlated with heparin concentration. The results are shown in FIG. 5.

In an alternative embodiment, a 2 µL assay was performed in a 1536 white Corning Costar plate as follows. 0.5 µL of peptide and ATP in CKII buffer was pipetted into each well followed by 0.5 µL of CKII in the same buffer and the reaction was allowed to proceed for 1 hr at 30° C. The final concentrations were 2.5 µM peptide, 200 µM ATP and 3.25 units/well of CKII. Then 1 µL of V8 protease was added resulting in 0.01 units protease per well. The reaction was allowed to go to completion by incubation at room temperature for 18 hrs. This yielded Z-factor of 0.55 in the RET signal which is suitable for high-throughput screening of chemical libraries (Zhang, Ji-Hu et al. (1999) J. Biol. Screening, 4: 67–73).

Phosphatase Assay

In another embodiment, the method of the present invention provides for measurement of phosphatase activity in a sample. For use in a phosphatase assay, a reporter peptide is synthesized with a phosphoamino acid within the protease recognition site. The presence of the phosphoamino acid within the protease recognition site prevents cleavage of the reporter peptide by the protease. Removal of the phosphate by exposure to a sample having phosphatase activity enables the protease to cleave the reporter peptide, thereby effecting a change in fluorescence. The level of protease activity is, therefore, directly proportional to the amount of phosphatase activity and can be measured by a change in fluorescence.

So, for example, a reporter peptide having a phosphoamino acid is prepared and labeled with a donor fluorophore and an acceptor molecule. When a donor fluorophore is held in close proximity to the acceptor molecule, the acceptor absorbs the light re-emitted by the donor fluorophore thereby quenching the fluorescence signal of the donor molecule while increasing the fluorescence of the acceptor molecule by energy-transfer. By monitoring at the wavelength at which the acceptor emits light, a decrease in fluorescence is observed when the peptide linking the two fluorophores is cleaved by the protease. Alternatively, if the donor wavelength is monitored, an increase in fluorescence is observed when the peptide linking the two fluorophores is cleaved by the protease. The level of phosphatase activity can then be measured using either the donor or the acceptor wavelength.

In another embodiment of the method when used as a phosphatase assay, the phosphorylated reporter peptide can be made to contain a fluorophore and a quencher molecule in close proximity. In this case, the re-emitted light from the fluorophore is quenched when the peptide is intact. Upon cleavage with the protease, an increase in fluorescence is observed. Hence, cleavage of the peptide and, therefore, increased fluorescence, is optimal in the presence of phosphatase activity. The level of fluorescence obtained, therefore, provides a direct indication of the level of phosphatase activity present in the sample.

In another embodiment of the method as a phosphatase assay, the phospho-reporter peptide can be made to contain a fluorophore and biotin. In this case, the fluorescence polarization of the peptide is measured by the addition of streptavidin after the phosphatase and protease reactions have been completed. Fluorescence polarization is proportional to the molecular weight; therefore, an increase in polarization signal will be observed when the biotinylated peptide containing the fluorophore binds to streptavidin. If, however, the fluorophore and biotin are separated by protease cleavage of the peptide, the fluorescence polarization does not increase upon the addition of streptavidin. Hence, the fluorescence polarization signal is inversely proportional to the level of phosphatase activity in the sample.

In another embodiment for a phosphatase assay, the phospho-reporter peptide contains lanthanides. In this embodiment, the reporter peptide is constructed by incorporating a lanthanide label at one end of a biotinylated phosphopeptide. A time-resolved fluorescence resonance energy transfer (TR-FRET) signal is obtained by the addition of allophycocyanin-labeled streptavidin as long as the biotinylated peptide contains the lanthanide. Once the lanthanide and the biotin are separated by protease cleavage, then the TR-FRET signal is decreased. Hence, the TR-FRET signal is indirectly proportional to the level of phosphatase activity in the sample.

In another embodiment of the phosphatase assay of the present invention, the phospho-reporter peptide contains a fluorophore and biotin. In this embodiment, the fluorophore is a cyanine dye and laser scanning confocal microscopy is used to image streptavidin micro-beads coated with the cyanine labeled biotinylated peptide. The fluorescent signal of each micro-bead is then quantified. If the cyanine is separated from the micro-bead by protease cleavage of the reporter peptide, the fluorescent signal of each bead is decreased. Hence, the fluorescent signal is indirectly proportional to the level of phosphatase activity in the sample.

TABLE 3

| Phosphatase | Reporter Peptide Molecule | Protease |
| --- | --- | --- |
| PTP generic | $(F_1)$-$X_n$-*Y-$X_n$-$(F_2)$(SEQ ID NO. 13) | chymotrypsin |
| PTP-1B | $(F_1)$-$X_n$-KDDE*YNPA-$X_n$-$(F_2)$(SEQ ID NO. 14)[a] | Endoprotease Glu-C or chymotrypsin |
| PP1 | $(F_1)$-$X_n$-RFDRR X'SV-$X_n$-$(F_2)$(SEQ ID NO. 15)[c] X' = V, I, L or F | Elastase |
| PP2A | $(F_1)$-$X_n$-RRREEEE*TEEE-$X_n$-$(F_2)$(SEQ ID NO. 16)[b] | Endoprotease Glu-C |
| PP2B(calcineurin) | $(F_1)$-$X_n$-RFDRR X'SV-$X_n$-$(F_2)$(SEQ ID NO. 15)[d] X' = V, I, L or F | Elastase |
| CamKPase | $(F_1)$-$X_n$-MHRQE*TVDX$_n$-$(F_2)$(SEQ ID NO. 17)[e] | Endoprotease Glu-C |

[a]Agostinis P. et al. (1996) Eur. J. Biochem. 236: 548–557;
[b]Agostinis P. et al. (1990) J. Biochem. 189: 235–241;
[c]Zhang L. et al. (1997) Biochemistry 36: 8209–8214;
[d]Sullivan, E. (1997) J.Biomol. Screening 2: 19–23.
[e]Ishida, A. (2001) J. Biochem. 129: 745–753.

Screening Test Compounds

The method of the present invention can be used to test for compounds that modulate kinase activity. Such modulators may include chemical compounds, for example, small molecules, mixtures of chemical compounds, biological macromolecules, or an extract made from biological materials such as bacteria, plants, fingi, or animal cells or tissues. Test compounds are evaluated for potential activity as agonists or antagonists of kinases by inclusion in the kinase assays described herein.

For example, a method for screening a substance for the ability to modulate kinase activity comprises the following steps. A portion of a kinase preparation is exposed to a test substance. The level of kinase activity in the preparation is then determined in accordance with the methods described herein. Briefly, the kinase preparation exposed to the test substance is incubated with a reporter peptide for an amount of time sufficient for phosphorylation of the peptide to occur; a protease capable of cleaving the reporter peptide in its unphosphorylated state is added and incubated for a time sufficient for proteolysis of the reporter peptide to occur. Finally, the level of kinase activity in the exposed kinase preparation is measured by detecting a change in a fluorescence characteristic of the reporter peptide whereby the change is indicative of kinase activity in the preparation and compared to an unexposed control.

The invention claimed is:

1. A method for measuring protein phosphatase activity in a sample, said method comprising the steps:
   (a) contacting said sample with a reporter peptide for an amount of time sufficient for dephosphorylation of the reporter peptide to occur, wherein said reporter peptide is a fluorescently labeled phosphorylated reporter peptide that is protease-cleavable when unphosphorylated;
   (b) contacting said sample with a protease which cleaves unphosphorylated reporter peptide for a time sufficient for proteolysis to occur; and
   (c) detecting a change in a fluorescence characteristic whereby said change indicates the level of phosphatase activity in the sample.

2. The method of claim 1 wherein said change in said fluorescence characteristic is selected from the group consisting of fluorescence intensity, fluorescence quenching (FQ), fluorescence polarization (FP), fluorescence resonance energy transfer (FRET), chemiluminescence-resonance energy transfer (CRET), bioluminescence resonance energy transfer (BRET) and time resolved fluorescence resonance energy transfer (TR-FRET).

3. The method of claim 1 wherein said change in said fluorescence characteristic is detected by a method selected from the group consisting of fluorescence microscopy, flow cytometry, fluorometry and absorption spectroscopy.

4. The method of claim 1 wherein said change in said fluorescence characteristic is detected using a fluorescence microplate reader.

5. The method of claim 1 wherein said peptide comprises an amino acid sequence selected from the group consisting of DE*SEEEDK (SEQ ID NO. 1) QKRP*SQR (SEQ ID NO.:2), RRRR*SIIFI (SEQ ID NO.: 3), $X_n$-*SP-$X_n$(SEQ ID NO.: 4), EEE*YEE (SEQ ID NO.: 5), K*SPXXXK (SEQ ID NO.: 6), EAVT*SPRFI (SEQ ID NO.: 7), HHHR*SPRKR (SEQ ID NO.: 8), HHHK*SPRRR (SEQ ID NO.: 9), KKRQQ*SFDMK (SEQ ID NO.: 10), $X_n$-H*SR-$X_n$-(SEQ ID NO.: 11), RFRR*SRRMI (SEQ ID NO.: 12), $X_n$-*Y-$X_n$ (SEQ ID NO. 13), $X_n$-KDDE*YNPA-$X_n$(SEQ ID NO. 14), Xn-RFDRRB*SV-$X_n$-(SEQ ID NO. 15), $X_n$-RRREEEE*TEEE-$X_n$ (SEQ ID NO. 16), $X_n$-MHRQE*TVDX$_n$(SEQ ID NO. 17), where B=V, I, L or F, *S is phosphoserine, *Y is phosphotyrosine, X is an amino acid, n is any number 0 or greater.

6. The method of claim 1 wherein said fluorescently labeled reporter peptide is selected from $(F_1)X_n$-DE*SEEEDK-$X_n(F_2)$(SEQ ID NO. 1), $(F_1)$-$X_n$-QKRP*SQR-$X_n$-$(F_2)$ (SEQ ID NO.:2), $(F_1)$-$X_n$-RRRR*SIIFI-$X_n$-$(F_2)$ (SEQ ID NO.: 3), $(F_1)$-$X_n$-EEE*YEE-$X_n$-$(F_2)$(SEQ ID NO.:) $X_n$-*SP-$X_n$(SEQ ID NO.: 4), $(F_1)$-$X_n$-K*SPXXXK-$X_n$-$(F_2)$ (SEQ ID NO.: 6), $(F_1)$-$X_n$-EAVT*SPRFI-$X_n$-$(F_2)$ (SEQ ID NO.: 7), $(F_1)$-$X_n$-HHHR*SPRKR-$X_n$-$(F_2)$ (SEQ ID NO.: 8), $(F_1)$-$X_n$-HHHK*SPRRR-$X_n$-$(F_2)$ (SEQ ID NO.: 9), $(F_1)X_n$-KKRQQ*SFDMK-$X_n$$(F_2)$ (SEQ ID NO.: 10), $(F_1)$-$X_n$-H*SR-$X_n$-$(F_2)$ (SEQ ID NO.: 11), $(F_1)$-$X_n$-RFRR*SRRMI-$X_n$-$(F_2)$ (SEQ ID NO.: 12), $(F_1)$-$X_n$-*Y-$X_n$-$(F_2)$ (SEQ ID NO. 13), $(F_1)$-$X_n$-KDDE*YNPA-$X_n$-$(F_2)$ (SEQ ID NO. 14), $(F_1)$-$X_n$-RFDRRX'*SV-$X_n$$(F_2)$ (SEQ ID NO. 15), $(F_1)$-$X_n$-

RRREEEE*TEEE-X$_n$-(F$_2$) (SEQ ID NO. 16), (F$_1$)-X$_n$-MHRQE*TVDX$_n$-(F$_2$) (SEQ ID NO. 17), where X'=V, I, L or F where*S is phosphoserine, *Y is phosphotyrosine, F$_1$ is a first fluorescent label, F$_2$ is a second fluorescent label, X is an amino acid, n is any number 0 or greater.

7. A method for screening a substance which modulates phosphatase activity comprising the steps:
  (a) exposing a first portion of a phosphatase preparation to said substance;
  (b) determining the level of phosphatase activity in said first portion by:
    (1) contacting said first portion with a reporter peptide for an amount of time sufficient for dephosphorylation of the reporter peptide to occur, wherein said reporter peptide is a fluorescently labeled phosphorylated reporter peptide that is protease-cleavable when unphosphorylated;
    (2) contacting said first portion with a protease which cleaves unphosphorylated reporter peptide for a time sufficient for proteolysis to occur; and
    (3) detecting a change in a fluorescence characteristic of said labeled reporter peptide wherein said change in fluorescence of said reporter peptide indicates phosphatase activity in said first portion;
  (c) repeating steps (1) through (3) for a second portion of the phosphatase preparation that has not been exposed to said substance and comparing the change in said fluorescence characteristic for said first and second portions wherein a difference in said change between said first and second portions indicates that said substance modulates said phosphatase activity.

8. The method of claim 7, further comprising the step of comparing the level of phosphatase activity in said preparation with a standard having a known level of phosphatase activity.

* * * * *

UNITED STATES PATENT AND TRADEMARK OFFICE
CERTIFICATE OF CORRECTION

PATENT NO. : 7,202,050 B2  Page 1 of 1
APPLICATION NO. : 11/100068
DATED : April 10, 2007
INVENTOR(S) : Douglas Auld It is certified that error appears in the above-identified patent and that said Letters Patent is hereby corrected as shown below:

In Claim 6:

Col. 26, line 58, delete "(SEQ ID NO.:)" and insert -- (SEQ ID NO.: 4) --

Col. 26, line 58, delete "(SEQ ID NO.: 4)" and insert -- (SEQ ID NO.: 5) --

Col. 26, line 62, delete "$(F_1)X_n$-" and insert -- $(F_1)$-$X_n$- --

Col. 26, line 63, delete "$X_n(F_2)$" and insert -- $X_n$ -$(F_2)$ --

Col. 26, line 67, delete "$X_n(F_2)$" and insert -- $X_n$ -$(F_2)$ --

Signed and Sealed this

Twenty-sixth Day of June, 2007

JON W. DUDAS
*Director of the United States Patent and Trademark Office*

SEQUENCE LISTING

<160> NUMBER OF SEQ ID NOS: 17

<210> SEQ ID NO 1
<211> LENGTH: 8
<212> TYPE: PRT
<213> ORGANISM: Artificial sequence
<220> FEATURE:
<221> NAME/KEY: SITE
<222> LOCATION: (1)..(8)
<223> OTHER INFORMATION: protease recognition site
<220> FEATURE:
<221> NAME/KEY: MISC_FEATURE
<222> LOCATION: (3)..(3)
<223> OTHER INFORMATION: serine at position 3 may be phosphorylated

<400> SEQUENCE: 1

Asp Glu Ser Glu Glu Glu Asp Lys
1               5

<210> SEQ ID NO 2
<211> LENGTH: 7
<212> TYPE: PRT
<213> ORGANISM: Artificial sequence
<220> FEATURE:
<221> NAME/KEY: SITE
<222> LOCATION: (1)..(7)
<223> OTHER INFORMATION: protease recognition site
<220> FEATURE:
<221> NAME/KEY: MISC_FEATURE
<222> LOCATION: (5)..(5)
<223> OTHER INFORMATION: serine in position 5 may be phosphorylated

<400> SEQUENCE: 2

Gln Lys Arg Pro Ser Gln Arg
1               5

<210> SEQ ID NO 3
<211> LENGTH: 9
<212> TYPE: PRT
<213> ORGANISM: Artificial sequence
<220> FEATURE:
<221> NAME/KEY: SITE
<222> LOCATION: (1)..(9)
<223> OTHER INFORMATION: protease recognition site
<220> FEATURE:
<221> NAME/KEY: MISC_FEATURE
<222> LOCATION: (5)..(5)
<223> OTHER INFORMATION: serine at position 5 may be phosphorylated

<400> SEQUENCE: 3

Arg Arg Arg Arg Ser Ile Ile Phe Ile
1               5

<210> SEQ ID NO 4
<211> LENGTH: 4
<212> TYPE: PRT
<213> ORGANISM: Artificial sequence
<220> FEATURE:
<221> NAME/KEY: SITE
<222> LOCATION: (1)..(4)
<223> OTHER INFORMATION: protease recognition site
<220> FEATURE:
<221> NAME/KEY: MISC_FEATURE
<222> LOCATION: (2)..(2)
<223> OTHER INFORMATION: serine at position 2 may be phosphorylated
<220> FEATURE:
<221> NAME/KEY: MISC_FEATURE
<222> LOCATION: (1)..(1)
<223> OTHER INFORMATION: x at position 1 may be any amino acid
<220> FEATURE:

-continued

```
<221> NAME/KEY: MISC_FEATURE
<222> LOCATION: (4)..(4)
<223> OTHER INFORMATION: x at position 4 may be any amino acid

<400> SEQUENCE: 4

Xaa Ser Pro Xaa
1

<210> SEQ ID NO 5
<211> LENGTH: 6
<212> TYPE: PRT
<213> ORGANISM: Artificial sequence
<220> FEATURE:
<221> NAME/KEY: SITE
<222> LOCATION: (1)..(6)
<223> OTHER INFORMATION: protease recognition site
<220> FEATURE:
<221> NAME/KEY: MISC_FEATURE
<222> LOCATION: (4)..(4)
<223> OTHER INFORMATION: tyrosine at position 4 may be phosphorylated

<400> SEQUENCE: 5

Glu Glu Glu Tyr Glu Glu
1               5

<210> SEQ ID NO 6
<211> LENGTH: 7
<212> TYPE: PRT
<213> ORGANISM: Artificial sequence
<220> FEATURE:
<221> NAME/KEY: SITE
<222> LOCATION: (1)..(7)
<223> OTHER INFORMATION: protease recognition site
<220> FEATURE:
<221> NAME/KEY: MISC_FEATURE
<222> LOCATION: (2)..(2)
<223> OTHER INFORMATION: Serine at position 2 may be phosphorylated
<220> FEATURE:
<221> NAME/KEY: MISC_FEATURE
<222> LOCATION: (4)..(6)
<223> OTHER INFORMATION: X at positions 4, 5 and 6 may be any amino acid

<400> SEQUENCE: 6

Lys Ser Pro Xaa Xaa Xaa Lys
1               5

<210> SEQ ID NO 7
<211> LENGTH: 9
<212> TYPE: PRT
<213> ORGANISM: Artificial sequence
<220> FEATURE:
<221> NAME/KEY: SITE
<222> LOCATION: (1)..(9)
<223> OTHER INFORMATION: protease recognition site
<220> FEATURE:
<221> NAME/KEY: MISC_FEATURE
<222> LOCATION: (5)..(5)
<223> OTHER INFORMATION: Serine at position 5 may be phosphorylated

<400> SEQUENCE: 7

Glu Ala Val Thr Ser Pro Arg Phe Ile
1               5

<210> SEQ ID NO 8
<211> LENGTH: 9
<212> TYPE: PRT
<213> ORGANISM: Artificial sequence
<220> FEATURE:
<221> NAME/KEY: SITE
<222> LOCATION: (1)..(9)
<223> OTHER INFORMATION: protease recognition site
```

```
<220> FEATURE:
<221> NAME/KEY: MISC_FEATURE
<222> LOCATION: (5)..(5)
<223> OTHER INFORMATION: Serine at position 5 may be phosphorylated

<400> SEQUENCE: 8

His His His Arg Ser Pro Arg Lys Arg
1               5

<210> SEQ ID NO 9
<211> LENGTH: 9
<212> TYPE: PRT
<213> ORGANISM: Artificial sequence
<220> FEATURE:
<221> NAME/KEY: SITE
<222> LOCATION: (1)..(9)
<223> OTHER INFORMATION: protease recognition site
<220> FEATURE:
<221> NAME/KEY: MISC_FEATURE
<222> LOCATION: (5)..(5)
<223> OTHER INFORMATION: Serine at position 5 may be phosphorylated

<400> SEQUENCE: 9

His His His Lys Ser Pro Arg Arg Arg
1               5

<210> SEQ ID NO 10
<211> LENGTH: 10
<212> TYPE: PRT
<213> ORGANISM: Artificial sequence
<220> FEATURE:
<221> NAME/KEY: SITE
<222> LOCATION: (1)..(10)
<223> OTHER INFORMATION: protease recognition site
<220> FEATURE:
<221> NAME/KEY: MISC_FEATURE
<222> LOCATION: (6)..(6)
<223> OTHER INFORMATION: Serine at position 6 may be phosphorylated

<400> SEQUENCE: 10

Lys Lys Arg Gln Gln Ser Phe Asp Met Lys
1               5                   10

<210> SEQ ID NO 11
<211> LENGTH: 4
<212> TYPE: PRT
<213> ORGANISM: Artificial sequence
<220> FEATURE:
<221> NAME/KEY: SITE
<222> LOCATION: (1)..(4)
<223> OTHER INFORMATION: protease recognition site
<220> FEATURE:
<221> NAME/KEY: MISC_FEATURE
<222> LOCATION: (3)..(3)
<223> OTHER INFORMATION: Serine at position 3 may be phosphorylated
<220> FEATURE:
<221> NAME/KEY: MISC_FEATURE
<222> LOCATION: (1)..(1)
<223> OTHER INFORMATION: X at position 1 may be any amino acid

<400> SEQUENCE: 11

Xaa His Ser Arg
1

<210> SEQ ID NO 12
<211> LENGTH: 9
<212> TYPE: PRT
<213> ORGANISM: Artificial sequence
<220> FEATURE:
<221> NAME/KEY: SITE
<222> LOCATION: (1)..(9)
```

```
<223> OTHER INFORMATION: protease recognition site
<220> FEATURE:
<221> NAME/KEY: MISC_FEATURE
<222> LOCATION: (5)..(5)
<223> OTHER INFORMATION: Serine at position 5 may be phosphorylated

<400> SEQUENCE: 12

Arg Phe Arg Arg Ser Arg Arg Met Ile
1               5

<210> SEQ ID NO 13
<211> LENGTH: 4
<212> TYPE: PRT
<213> ORGANISM: Artificial sequence
<220> FEATURE:
<221> NAME/KEY: SITE
<222> LOCATION: (1)..(4)
<223> OTHER INFORMATION: protease recognition site
<220> FEATURE:
<221> NAME/KEY: MISC_FEATURE
<222> LOCATION: (2)..(2)
<223> OTHER INFORMATION: Tyrosine at position 2 is  phosphorylated
<220> FEATURE:
<221> NAME/KEY: MISC_FEATURE
<222> LOCATION: (1)..(1)
<223> OTHER INFORMATION: X at position 1 is any amino acid
<220> FEATURE:
<221> NAME/KEY: MISC_FEATURE
<222> LOCATION: (3)..(4)
<223> OTHER INFORMATION: X at positions 3 and 4 are any amino acid

<400> SEQUENCE: 13

Xaa Tyr Xaa Xaa
1

<210> SEQ ID NO 14
<211> LENGTH: 8
<212> TYPE: PRT
<213> ORGANISM: Artificial sequence
<220> FEATURE:
<221> NAME/KEY: SITE
<222> LOCATION: (1)..(8)
<223> OTHER INFORMATION: protease recognition site
<220> FEATURE:
<221> NAME/KEY: MISC_FEATURE
<222> LOCATION: (5)..(5)
<223> OTHER INFORMATION: Tyrosine at position 5 is phosphorylated

<400> SEQUENCE: 14

Lys Asp Asp Glu Tyr Asn Pro Ala
1               5

<210> SEQ ID NO 15
<211> LENGTH: 8
<212> TYPE: PRT
<213> ORGANISM: Artificial sequence
<220> FEATURE:
<221> NAME/KEY: SITE
<222> LOCATION: (1)..(8)
<223> OTHER INFORMATION: protease recognition site
<220> FEATURE:
<221> NAME/KEY: MISC_FEATURE
<222> LOCATION: (7)..(7)
<223> OTHER INFORMATION: Serine at position 7 is phosphorylated
<220> FEATURE:
<221> NAME/KEY: MISC_FEATURE
<222> LOCATION: (6)..(6)
<223> OTHER INFORMATION: Xaa at position 6 is preferably Val, Ile, Leu,
      or Phe

<400> SEQUENCE: 15

Arg Phe Asp Arg Arg Xaa Ser Val
```

```
<210> SEQ ID NO 16
<211> LENGTH: 11
<212> TYPE: PRT
<213> ORGANISM: Artificial sequence
<220> FEATURE:
<221> NAME/KEY: SITE
<222> LOCATION: (1)..(11)
<223> OTHER INFORMATION: protease recognition site
<220> FEATURE:
<221> NAME/KEY: MISC_FEATURE
<222> LOCATION: (8)..(8)
<223> OTHER INFORMATION: Threonine at position 8 is phosphorylated

<400> SEQUENCE: 16

Arg Arg Arg Glu Glu Glu Glu Thr Glu Glu Glu
1               5                   10

<210> SEQ ID NO 17
<211> LENGTH: 8
<212> TYPE: PRT
<213> ORGANISM: Artificial sequence
<220> FEATURE:
<221> NAME/KEY: SITE
<222> LOCATION: (1)..(8)
<223> OTHER INFORMATION: protease recognition site
<220> FEATURE:
<221> NAME/KEY: MISC_FEATURE
<222> LOCATION: (6)..(6)
<223> OTHER INFORMATION: Threonine at position 6 is phosphorylated

<400> SEQUENCE: 17

Met His Arg Gln Glu Thr Val Asp
1               5
```